US006620628B2

(12) United States Patent
Sutton et al.

(10) Patent No.: US 6,620,628 B2
(45) Date of Patent: Sep. 16, 2003

(54) ANALYTICAL ELEMENTS HAVING A SURFACE CHARGE

(75) Inventors: Richard Sutton, Rochester, NY (US); Susan Danielson, Honeoye Falls, NY (US); Jerome Swartz, Rochester, NY (US); Linda Mauck, Rochester, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 0 days.

(21) Appl. No.: 09/797,817

(22) Filed: Mar. 2, 2001

(65) Prior Publication Data

US 2002/0009732 A1 Jan. 24, 2002

Related U.S. Application Data

(60) Provisional application No. 60/186,577, filed on Mar. 2, 2000.

(51) Int. Cl.[7] ............... G01N 33/545; G01N 33/553; G01N 33/532
(52) U.S. Cl. ................. 436/531; 436/525; 436/535; 436/544; 436/805; 436/815; 436/826
(58) Field of Search ................. 436/525, 546, 436/531, 535, 826, 815, 544, 805

(56) References Cited

U.S. PATENT DOCUMENTS

| | | | | |
|---|---|---|---|---|
| 4,153,668 A | * | 5/1979 | Hill et al. | |
| 4,283,382 A | * | 8/1981 | Frank et al. | |
| 4,547,460 A | | 10/1985 | Eikenberry | |
| 5,094,962 A | * | 3/1992 | Snyder et al. | |
| 5,268,097 A | | 12/1993 | Girot et al. | |
| 5,279,940 A | * | 1/1994 | Kissel | |
| 5,459,078 A | * | 10/1995 | Kline et al. | |
| 5,643,721 A | * | 7/1997 | Spring et al. | |
| 5,705,353 A | | 1/1998 | Oh et al. | |
| 5,789,261 A | * | 8/1998 | Schwartz | |

FOREIGN PATENT DOCUMENTS

| | | | |
|---|---|---|---|
| EP | 0347137 A2 | | 12/1989 |
| EP | 0889327 A | | 1/1990 |
| EP | 0786666 A | | 7/1997 |
| GB | 2233451 | * | 1/1991 |
| WO | WO 90/10229 A | | 9/1990 |
| WO | WO 93/07298 A | | 4/1993 |

OTHER PUBLICATIONS

EPO Search Report for EP 01 30 1868, mailed Jun. 6, 2002.

* cited by examiner

Primary Examiner—Mary E. Ceperley
(74) Attorney, Agent, or Firm—Todd F. Volyn

(57) ABSTRACT

An assay element for analyzing a charged analyte employs an immobilized receptor and a material having a net charge which is the same as that of the analyte. In a preferred embodiment, the analyte is an aminoglycoside and the material is a polymer having a net positive charge.

16 Claims, No Drawings

ANALYTICAL ELEMENTS HAVING A SURFACE CHARGE

This application claims the benefit of U.S. Provisional Application No. 60/186,577, filed Mar. 2, 2000.

BACKGROUND OF THE INVENTION

This invention relates to the analysis of analytes having a net charge or their derivatives of analytes having a net charge.

Immunoassays can be used to determine the presence and quantity of a range of analytes including antigens, antibodies, therapeutic drugs, narcotics, enzymes, hormones, and proteins. Their specificity gives these assays particular utility in clinical chemistry. A variety of media are available for performing such assays including, for example, dry immunoassay elements such as multicomponent slides; microtiter plates; "dip and read" test strips; bead and tube tests; and microparticles. The different configurations of the immunoassay kits in which the assay is performed are referred to herein as analytical elements. They can comprise, among many others, a bead onto which an antibody is adhered ("immobilized") to serve as a receptor, a cup having a surface for similar use, or a polymer layer within a slide onto which sample and reagent are applied, spread, and reacted.

In these assays, conjugate pairs are formed from either analyte ("ligand") and receptor combinations or labeled analyte ("labeled ligand") and receptor combinations. In competitive binding immunoassays, labeled ligand competes with unlabeled ligand for reaction with a fixed amount of a particular receptor. Signal measurements such as light absorbance or reflection density are taken of either the bound or unbound labeled ligand after appropriate treatment with various reagents such as chromophores or flourometrically sensitive materials. Unknown ligand concentration is then determined from the measured signal of the labeled ligand after removing (e.g., by washing away) the other species that are not useful for calculating ligand concentration. Thus, it is important to have a reliable method to separate properly bound and unbound forms of ligands or labeled ligands. Failure to do so can lead to inaccurate or imprecise results.

In actual practice, signal measurements can be obtained from labeled ligand, a labeled derivative or analog of the ligand, or a labeled receptor which binds in a specific manner to a ligand as in the case of a sandwich assay.

In general, ligands that are capable of binding non-specifically to, for example, hydrophobic sites and/or ligands that possess a net charge and are capable, therefore, of binding non-specifically to oppositely charged centers are particularly problematic in analytical systems. In such cases, a step may be required to separate free from bound species. That is, they tend to bind to components of assay elements while their labeled counterparts bind to receptors. This makes separation of bound and unbound species incomplete. The same can be said of the labeled ligand when it is the unlabeled ligand that is sought to be bound to the receptor. Aminoglycosides such as gentamicin and tobramycin are two amine rich analytes that possess a net positive charge under conditions in which one or more of the amine groups is protonated—generally below about pH 11. These analytes are particularly important and yet immunochemical methods of quantitatively measuring them are vulnerable to the inaccuracy and imprecision described above. It is particularly desirable to improve methods for measuring these analytes and others like them.

U.S. Pat. No. 4,547,460 proposes the use of quarternary ammonium compounds as additives for elements of an immunoassay. The ammonium compounds are used to reduce interference from bilirubin and proteins. Presumably, such interference is reduced as a result of complexing bilirubin and/or proteins with the quarternary ammonium compounds. Of course, this can only occur where the bilirubin or protein have a different charge than the ammonium compound.

U.S. Pat. No. 5,279,940 proposes the use of cationic surfactants as signal enhancers in chemiluminescene-based analytical elements. The surfactant is part of the mix of components that provides the enhanced signal. It is not involved in removing substances whose presence would otherwise generate a signal leading to an inaccurate result.

U.S. Pat. No. 4,153,668 proposes using positively charged polymers in an analytical element to more uniformly disperse a liquid containing a negatively charged analyte (a protein bound or proteinaceous substance). The patent discloses only the use of polymers having a net charge that is opposite that of the analyte.

Immunoassay accuracy and precision can still be improved where the analyte has a net charge.

SUMMARY OF THE INVENTION

The invention is an assay element for analyzing a charged analyte. The assay element employs an immobilized receptor and a material having a net charge which is the same as that of the analyte.

In one aspect of the invention the analyte is amine rich and the material is a polymer having a net positive charge and the analysis in which the element is used is a competitive binding immunoassay.

In yet another aspect of the invention, the element is a polymer having a net charge such as poly(acrlyamide-co-N-(3-methacrylamidopropyl)-N,N,N-trimethylammonium chloride.

DETAILED DESCRIPTION OF THE INVENTION

Immunoassays for analytes having a net charge can be improved by the incorporation of a suitable substance possessing the same net charge into analytical element for determining the presence or amount of the analyte. By the same net charge, it is meant that if an analyte possesses a net positive (negative) charge then the substance possesses a net positive (negative) charge, but they are not required to possess the same quantity of charge. By way of illustration, if an analyte possesses a net charge of +2, the substance must possess a net positive charge, but it is not required to be a net charge of +2. It can be any positive charge. Such an element acts to prevent ligand and/or labeled-ligand from adhering nonspecifically. This enhances accuracy and precision in, for example, competitive binding assays resulting in the production of a signal more truly representative of the true concentration of analyte in a sample.

In the assays of this invention, a receptor such as an antibody is generally immobilized in or on a component of the analytical element comprising a material having a net charge that is the same as that of the analyte. The element can be a layer of film; the surface of a cup; a fibrous layer used, for example, in "dip and read" format; a bead; a tube surface; or other medium. The receptor is specific for the analyte having the net charge. Either before the receptor is bound to the element or after the receptor is immobilized on an analytical element, sample containing the analyte is added to it. The analyte may have been previously mixed with labeled-analyte. Alternatively, the labeled-analyte could be added later. In any case, analyte and labeled analyte will then compete with each other for sites on the receptor. Because the component of the assay element to which the receptor is bound and/or some other component or surfaces nearby or in contact with the component of the element of the analytical device also has a net charge that is the same as the ligand or labeled ligand, the species which is not meant to be preferentially bound to the receptor will be repelled by the element to which it is affixed. In a subsequent step in which the species not meant to be bound is to be removed (e.g., by washing), it is not able to nonspecifically bind to the element. Accordingly, it is more readily removed from the assay. Thus, in a yet further step in which the bound ligand or bound labeled ligand is exposed to further reagents such as enzyme substrate and then measured for the generation of a signal, there is a reduced level of nonspecifically bound ligand or labeled ligand to generate such an undesirable signal. This results in an analyte measurement that is more accurate and more precise. Alternatively, the label that has been separated from that which is specifically bound to the receptor can be measured with greater accuracy and precision. This assay could also be performed in an inverse format whereby the analyte (ligand) is bound directly or indirectly to the element and the receptor is labeled. Non-specific binding would still be a problem here, and the addition of a charged polymer would also ameliorate this situation.

Materials useful as the charge bearing substance of this invention include any material to which a receptor can be immobilized and which is capable of carrying a net charge. The substance is not limited to a material that is capable of binding a receptor but it must be capable of bearing a charge. These materials include, for example, metals, ceramics, zeolites, organic polymers, inorganic polymers, oligomers, macromers, ionomers, and semiconductors. Polymers are preferred. Water soluble polymers are more preferred.

The most preferred polymers of this invention are copolymers comprised of cationic vinyl monomers that undergo addition polymerization. For clarity, the term "copolymer" is used to mean any polymer formed by the combination of two or more non-identical monomers and includes species such as terpolymers and the like. Preferably, copolymer compositions used in the invention comprise 20–80% wt (based on total weight) of copolymer of cationic species with the remainder being a diluent comonomer. Cationic vinyl addition monomers comprising quaternary nitrogens having alkyl substituents of one to three carbon atoms have been found suitable when the analyte has a net positive charge as with aminoglycosides. Those having quaternary nitrogen containing groups having carbon, hydrogen, and hetero atoms necessary to complete a substituted or unsubstituted mono or polycylic nitrogen-containing cationic group having about 5–14 ring carbon and hetero atoms have also been found to be particulary suitable in similar circumstances.

In a preferred embodiment, the polymer is made from a monomer that includes a quaternary nitrogen having one or more $C_1$ to $C_3$ alkyl groups, or a monomer having a mono- or poly-cyclic ring between 5 to 14 ring atoms selected from C, S, N, or O, provided at least one of the ring atoms is a quaternary nitrogen.

The following are particularly suitable monomers for the copolymers used to make the analytical elements of this invention. 1-(N,N,N-trimethylammonium)ethyl methacrylate chloride, 2-(N,N,N-trimethylammonium)ethyl acrylate methosulfate, 3-(N,N,N-trimethylammonium-2-hydroxy) propyl methacrylate methosulfate, N-(2-acryloyloxyethyl)-N,N-dimethyl-N-ethylammonium ethosulfate, 2-(N,N,N-trimethylammonium)ethyl methacrylate methosulfate, 3-(N,N,N-trimethylammonium-2-hydroxy)propyl methacrylate chloride, N-(2-acryloyloxyethyl)-N,N-dimethyl-N-ethyl-ammonium chloride, 3-trimethylammonio-1,1-dimethylpropylacrylamide methosulfate, 3-methyl-1-vinylimidazolium methosulfate, m&p-N-vinylbenzyl-N,N-dimethyl-N-cyclohexylammonium chloride (60:40), 4-vinyl-N-methylpyridinium methosulfate, m&p-N-vinylbenzyl-N,N,N-triethylammonium chloride, m&p-N-vinylbenzyl-N,N,N-trimethylammonium chloride (60:40), m&p-N-vinylbenyl-N-benzyl-N,N-dimethylammonium chloride (60:40), m&p-N-vinylbenzylpyridinium chloride (60:40), 2-(N,N,N-trimethylammonium)ethyl methacrylate chloride, N-(2-acryloyloxyethyl)-N,N,N-triethylammonium ethosulfate, and 3-(N,N,N-trimethylammonium-2-hydroxy) propyl methacrylate chloride.

Preferred monomers are of the formula:

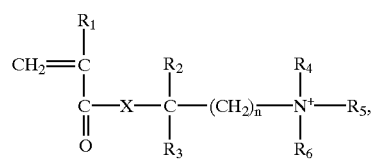
(I)

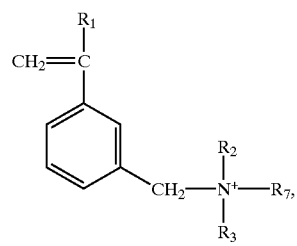
(II)

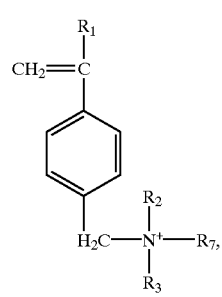
(III)

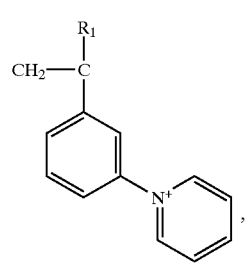
(IV)

-continued

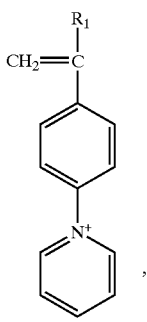

(V)

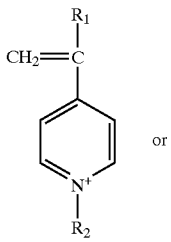

or (VI)

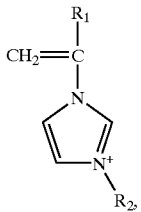

(VII)

and a monomer of formula

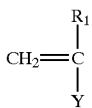

(VIII)

wherein X is NH or O; $R_1$ is H or $CH_3$; $R_2$, $R_3$, $R_4$, $R_5$ and $R_6$ are independently H, $CH_3$, $CH_2CH_3$, $R_7$ is H, $CH_3$, $CH_2CH_3$ or cyclohexyl; Y is $CONHCH_2CH_2CH_3$, $CONHCH(CH_3)_2$, $COOCH_2CH_2OH$, or 2-pyrrolidinone-1-yl; and n is 0, 1 or 2.

Diluent monomers are vinyl addition monomers, typically hydrophilic non-ionic acrylamides or methacrylamides or acrylates or methacrylates. A preferred diluent monomer is acrylamide. Other diluent monomers include but are not limited to N-isopropylacrylamide, 2-hydroxyethyl acrylate, 2-hydroxyethyl methacrylate, and N-vinyl-2-pyrrolidone.

The most preferred copolymer is poly(acrylamide-co-N-(3-methacrylamidopropyl)-N,N,N-trimethylammonium chloride (50/50) wt ratio.

The copolymers of this invention can be prepared using standard emulsion, solution, or suspension polymerization techniques. Numerous patent and non-patent publications are available to the skilled artisan describing polymerization methods useful for preparing copolymers of this invention, for example: Sorenson et al. in *Preparative Methods of Polymer Science*, 2$^{nd}$ Ed. Wiley and Sons (1968); Stevens, *Polymer Chemistry, An Introduction*, Addison Wesley Publishing Co. (1975); U.S. Pat. Nos. 4,581,314 and 4,599,389, and 4,201,840. The entire contents of these publications are incorporated herein by reference. U.S. Pat. No. 4,201,840 for example, teaches the preparation of poly acrylamide-co-N-(3-methacrylamidopropyl)-N'-(3-chloroprop ionyl)urea by first preparing a solution of 36 g of acrylamide, 9 g of N-(3-methacrylamidopropyl)-N'-(3-chloropropionyl)urea, and 225 mg of 2,2'-azobis(2-methylpropionitrile) in 405 ml of dimethylsulfoxide. The solution was flushed with nitrogen for ½ hour and heated at 60° C. overnight to yield a viscous polymer solution. The polymer was isolated by precipitation from acetone, collected by filtration and dried. The desired polymers of this invention can be made in similar fashion. A specific relative amount of one monomer to another monomer in the copolymer can be obtained by using that specific relative amount of each monomer at the start of the polymerization reaction.

In the dry-film immunoassay elements of the present invention, the cationic polymers may be incorporated as a separate layer between the receptor layer (reaction zone) and the spread layer; in the receptor layer; in the spread layer; or in a gravure layer over the spread layer. The polymer may be applied as gravure layer in multiple passes. A gravure layer, as the term is used in this specification, is a layer disposed on the surface of another layer (such as a spread layer) that does not substantially penetrate the layer on which it is disposed. Applying the polymer as a gravure layer in multiple passes is particularly desirable where the polymer is applied as part of a dilute polymer solution. A preferred method is to incorporate the polymer both in the receptor layer and in the gravure layer. The amount of polymer to be incorporated in the coated element may vary from 0.2–2.5 g/m$^2$, a preferred coverage is 0.8 g/m$^2$ (incorporated into the receptor and gravure layer). Incorporation of dry film analytical elements and their construction is taught, for example, in U.S. Pat. No. 4,258,001, No. 4,357,363, No. 5,714,340 and No. 5,928,886; each of which is incorporated herein by reference. Essentially, a plastic film support comprising a material such as polyethylene terephthalate is coated with various layers by the addition of wet slurries. In the case of the charged polymers of this invention, the wet slurry can be worked at room temperature. It is applied to a thickness of preferably about 0.1 to about 1.0 g/m$^2$ (more preferably about 0.2–0.4 g/m$^2$) (based on dry coverage) and air dried.

When the charged polymer is incorporated into the receptor layer, the microgel polymer used in the receptor layer and the charged polymer are combined (along with the additional ingredients used in such layers) with deionized, distilled water and the pH is adjusted to 7.0. The wet coverage of the receptor melt is 45 g/m$^2$. The melt is coated while at room temperature and is dried at elevated temperature, preferably about 95° C.

When the charged polymer is incorporated into the element as a separate layer, the melt is prepared as described above for the receptor layer except that the antibody beads, the micorgel polymer, and the leuco dye are omitted.

The following nonlimiting examples further illustrate the invention.

EXAMPLE 1

Preparation of Polymer 1, Poly[(N-isopropylacrylamide-co-N-(3-methyacrylamidopropyl)-N,N,N-trimethylammonium Chloride] (50:50 wt. Ratio)

125 g of N-isopropylacrylamide (Aldrich):

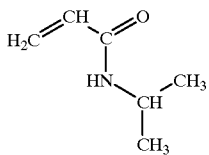

and 250 g of 50% N-(3-methyacrylamidopropyl)-N,N,N-trimethylammonium chloride (Aldrich):

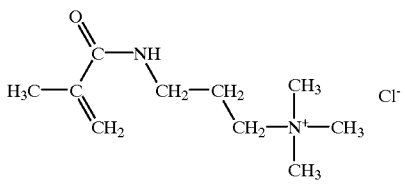

in water were combined with 1660 mL of deionized, distilled water in a 2 L flask. The resulting slurry was stirred at room temperature for 15 minutes. The resulting clear, colorless solution was filtered through Whatman GF/F filter paper (2.7 □). The solution was sparged with nitrogen for 15 minutes and was transferred to a 3 L 3-neck flask. A catalyst solution was prepared by dissolving 2.5 g $K_2S_2O_8$ and 0.5 g $Na_2S_2O_5$ in 50 mL of deionized, distilled water with 10 minutes of stirring at room temperature. The catalyst solution was added to the monomer solution. The flask was fitted with a stirring apparatus, condenser and $N_2$ inlet and was placed in an 80° C. bath and stirred under $N_2$ for 18 hours at 200 rpm. The reaction was then cooled to room temperature and vacuum filtered through Whatman GF/F filter paper (2.7μ). The resulting product contained 12.3% solids.

EXAMPLE 2

Preparation of Polymer 2, Polyl[(Acrylamide)-co-N-(3-methyacrylamidopropyl)-N,N,N-trimethylammonium Chloride] (50:50 wt. Ratio)

125 g of Acrylamide (Aldrich):

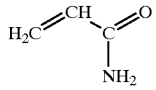

and 250 g of 50% N-(3-methyacrylamidopropyl)-N,N,N-trimethylammonium chloride (Aldrich), as shown above for Polymer 1, in water were combined with 1533 mL of deionized, distilled water in a 2 L flask. The resulting slurry was stirred at room temperature for 15 minutes. A clear, colorless solution resulted. The solution was sparged with nitrogen for 15 minutes and was transferred to a 3 L 3-neck flask. A catalyst solution was prepared by dissolving 2.5 g $K_2S_2O_8$ and 0.5 g $Na_2S_2O_5$ in 50 mL of deionized, distilled water with 10 minutes of stirring at room temperature. The catalyst solution was added to the monomer solution. The flask was fitted with a stirring apparatus, condenser and $N_2$ inlet and was placed in an 80° C. bath and stirred under $N_2$ for 18 hours at 200 rpm. The reaction was then cooled to room temperature. A moderately viscous pale yellow solution resulted. The resulting product contained 13.2% solids.

EXAMPLE 3

Performance of Gentamicin Elements Comprising A Cationic Polymer

Two cationic polymers were employed as analytical elements for a gentamicin assay. Polymer 1 was (poly(N-isopropylacrylamide-co-N-(3-methacrylamidopropyl)-N,N,N-trimethylammonium chloride (50/50) wt ratio) and polymer 2 was (poly(acrylamide-co-N-(3-methacrylamidopropyl)-N,N,N-trimethylammonium chloride (50/50) wt ratio). A standard element was employed for comparison. The assay was formulated as a dry-film immunoassay according to the method described in U.S. Pat. No. 4,357,363, incorporated herein by reference. Components are shown below.

Three different films were prepared. In each case, the components were the same except that the subbing zone in Element A (not according to the invention) contained no positively charged polymer. The subbing zone in Element B was prepared with 0.4 $g/m^2$ poly(N-isopropylacrylamide-co-N-(3-methacrylamidopropyl)-N,N,N-trimethylammonium chloride (50/50 wt ratio based on weights of each monomer unit) (polymer 1). The subbing zone in Element C was prepared with 0.4 $g/m^2$ poly(acrylamide-co-N-(3-methacrylamidopropyl)-N,N,N-trimethylammonium chloride (50/50) wt ratio (polymer 2).

Coatings Compared in Example 3

| Component | Dry Coverage ($g/m^2$) |
| --- | --- |
| 4) Bead Spreading Layer | |
| TES, pH 7.0 | .219 |
| 3', 5'-dichloroacetanilide | .220 |
| Dimedone | .450 |
| Poly(methyl acrylate-co-2-acrylamido-2-methylpropane sulfonic acid, sodium salt-co-2-acetoacetoxyethyl methacrylate) (90/4/6) wt (latex 1) | 2.583 |
| Poly (m-& p vinyltoluene (64:36)-co-methacrylic acid) beads | 130 |
| Bovine gamma globulin | 1 |
| Glycerol | 2 |
| Mannitol | 1 |
| Vanadyl sulfate | .040 |
| 3) Subbing Zone-as described above | |
| 2) Receptor Layer | |
| TES, pH 7.0 | .10 |
| TRITON TX-100 | .02 |
| Triarylimidazole leuco dye dispersion | .20 |
| Anti-gentamicin beads | .10 |
| Polymer Microgel A | 0.5 |
| 1) Gelatin Layer | |
| Gelatin | 10 |
| TES, pH 7.0 | 4.58 |
| 3',5'-dichloroacetanilide | .44 |

-continued

| Component | Dry Coverage (g/m²) |
|---|---|
| TRITON TX-100 | .02 |
| Bis (vinylsulfonylmethyl) ether hardener (BVSME) | .15 |

Polymer Microgel A is poly(N-isopropylacrylamide-co-2-hydroxyethyl methacrylate-co-methylene bis(acrylamide) (85/5/10)wt ratio.

TES is N-Tris(hydroxymethyl)-methyl-2-aminoethanesulfonic acid.

TRITON X 100 is octylphenoxy polyethoxyethanol available from Sigma Chemical.

A series of human serum-based calibrator fluids comprising gentamicin and a label prepared from a gentamicin analog covalently attached to horseradish peroxidase (gentamicin*-HRP) was prepared. The serum based calibrator fluids contained gentamicin in concentrations ranging from 0 to 14.2 µg/mL. The gentamicin*-HRP label was added to give a final concentration of 1.5 nM in the calibrator fluid for the coating which contained no cationic polymer and a final concentration of 3.0 nM for the coatings which contained polymer 1 or polymer 2. Previous testing (data not included) showed that a lower label concentration was necessary for elements which contained no cationic polymer because of poor washout and resulting high background rates.

An aliquot of serum-based fluid (11 µL) was spotted directly onto the bead spread layer of the dry-film element. The element was then incubated for 5 minutes at 37° C. A wash fluid (12 µL) containing sodium phosphate buffer (10 mM, pH=6.8), 4'-hydroxyacetanilide (5 mM), hydrogen peroxide (0.03% v/v), hexadecylpyridinium chloride (0.1% w/v), and diethylenetriaminepentaacetic acid (10 mM) was then applied to the element slowly over a 15.4 second interval to wash away free label from the detection area, and to initiate HRP catalyzed color formation on the "VITROS 250" chemistry system commercially available from Ortho Clinical Diagnostics. The element was then placed in a 37° C. incubator, and reflectance density (Dr) readings were taken every three seconds at 670 nm. The Dr values were converted to Dt using the Clapper-Williams transform. The change in Dt over 60 seconds was calculated. The results are shown below:

| | Rate (Dt/min) | | |
|---|---|---|---|
| Gentamicin (µg/mL) | Element A (No Polymer) | Element B (Polymer 1) | Element C (Polymer 2) |
| 0 | 0.217 | 0.176 | 0.248 |
| 0.7 | 0.205 | 0.158 | 0.204 |
| 1.2 | 0.191 | 0.138 | 0.163 |
| 3.2 | 0.148 | 0.094 | 0.088 |
| 5.3 | 0.117 | 0.069 | 0.057 |
| 7.6 | 0.098 | 0.056 | 0.042 |
| 10.4 | 0.078 | 0.043 | 0.032 |
| 14.2 | 0.063 | 0.038 | 0.027 |

Both elements (B and C) prepared with the cationic polymers (1 and 2) show a larger change of rate (steeper slope) at low levels of gentamicin. The change in rate between 0 and 3.2 µg/mL gentamicin is −0.069, −0.082, and −0.160 Dt/min for elements A, B, and C respectively.

Both of the elements that contain cationic polymer show substantially lower background rates in the presence of a high concentration of gentamicin even though both were tested in the presence of twice as much label as the no polymer element (3 nM vs 1.5 nM). The rates obtained with the fluid which contained the highest level of gentamicin (14.2 µ/mL) were 0.063, 0.038, and 0.027 Dt/min for elements A, B, and C respectively.

EXAMPLE 4

Effect of Location of Cationic Polymer on Performance (Dose Response Curve)

Gentamicin assay elements were prepared as described in Example 1. They comprised the cationic polymer 2 either directly in the receptor layer (Element D), or in a gravure layer deposited directly on the spread layer at a dry coverage of 0.2 g/m² (Element E). These elements were compared to an element which contained 0.4 g/m² polymer 2 incorporated as a subbing layer located between the receptor and spreading layer as described in Example 1 (Element C). An element which did not contain any cationic copolymer as described in Example 1 was also tested (Element A). All four elements contained gentamicin*-HRP incorporated into the element in the gravure process either at 0.000024 g/m² (elements comprising polymer 2) or at 0.000012 g/m² in the element which did not contain polymer 2.

Coatings Compared in Example 4

| Component | Dry Coverage (g/m²) |
|---|---|
| 5) Gravure Layer | |
| Gentamicin*-HRP | .000012or.000024 |
| MOPS, pH 7.0 | .0045 |
| Bovine Serum Albumin | .000215 |
| Polyacrylamide | .00108 |
| TRITON TX-100 | .0043 |
| 3',5'-dichloroacetanilde | .00995 |
| Carboxymethylated-apo-HRP | 0.010 |
| Magenta Dye | .0538 |
| polymer 2* | .20 |
| 4) Bead Spreading Layer | |
| TES, pH 7.0 | .219 |
| 3'5'-dichloroacetanilide | .220 |
| Dimedone | .450 |
| (latex 1) | 2.583 |
| Poly (m-& p vinyltolune (64:36)-co-methacrylic acid) beads | 130 |
| Bovine Serum Albumin | 1 |
| Glycerol | 2 |
| Mannitol | 1 |
| Vanadyl sulfate | .040 |
| 3) Subbing Zone* | |
| polymer 2* | |
| 2) Receptor Layer | |
| TES, pH 7.0 | .10 |
| TRITON TX-100 | .02 |
| Triarylimidazole leuco dye dispersion | .20 |
| *polymer 2 | .40 |
| Anti-gentamicin beads | .10 |
| polymer microgel A | 0.5 |
| 1) Gelatin Layer | |
| Gelatin | 10 |
| TES, pH 7.0 | 4.58 |

-continued

| Component | Dry Coverage (g/m$^2$) |
|---|---|
| 3',5'-dichloroacetanilide | .44 |
| TRITON TX-100 | .02 |
| BVSME hardner | .15 |

*Four coatings were prepared:
Element A (not according to the invention) did not contain any cationic polymer
Element C contained 0.40 g/m$^2$ polymer 2 in layer 3 (Subbing zone)
Element D contained 0.40 g/m$^2$ polymer 2 in layer 2 (Receptor Layer)
Element E contained 0.20 g/m$^2$ polymer 2 in layer 5 (Gravure Layer)
MOPS is 3-(4-Morpholino)propanesulfonic acid MOPS is 3-(4-Morpholino)propanesulfonic acid These elements were tested with the serum based calibrator fluids described in Example 1; however, gentamicin*-HRP was not added to the calibrator fluids because the label was incorporated directly into the element. The elements were tested as described in Example 1. The results are shown below:

| Gentamicin (μg/mL) | Element A (no polymer) | Element C (polymer 2 in Sub) | Element D (polymer 2 in Rec.) | Element E (polymer 2 in gravure) |
|---|---|---|---|---|
| 0 | 0.241 | 0.281 | 0.247 | 0.307 |
| 0.7 | 0.223 | 0.229 | 0.196 | 0.262 |
| 1.2 | 0.206 | 0.187 | 0.157 | 0.216 |
| 3.2 | 0.152 | 0.110 | 0.093 | 0.131 |
| 5.3 | 0.115 | 0.082 | 0.071 | 0.092 |
| 7.6 | 0.096 | 0.068 | 0.061 | 0.075 |
| 10.4 | 0.076 | 0.062 | 0.055 | 0.064 |
| 14.2 | 0.064 | 0.058 | 0.052 | 0.058 |

All three elements prepared with the cationic polymer 2 (Elements C, D, and E) show an increased rate of change over the concentration range of gentamicin tested compared with the element which does not contain polymer 2 (Element A).

Element E (prepared with polymer 2 in the gravure layer) shows the greatest rate of change over the concentration range of gentamicin tested.

Elements D and E offer and additional advantage in that there is no need to coat a separate layer which containing the cationic polymer. In these elements, the cationic polymer was incorporated via the gravure process which is a preferred method of incorporating the labeled analyte.

EXAMPLE 5

Comparison of the Performance of Elements A, D, and E Using Patient Samples

Three of the elements described in Example 3 (A, D, and E) were evaluated using 50 patient serum samples in which the amount of gentamicin in each sample was determined using the COBAS FP fluorescence polarization immunoassay commercially available from Roche Diagnostics. A calibration curve was generated for each element by relating the observed rates measured as described in Example 1 to gentamicin concentration using as reference values the amount of gentamicin in the serum samples as determined using the COBAS method. The concentrations of all the samples were then estimated from this calibration curve. The estimated concentrations of each sample obtained with each element were compared to the COBAS FP reference values using a best fit straight line regression analysis. The results are shown below:

| | R$^2$ | Sy.x |
|---|---|---|
| Element A | 0.963 | 0.486 |
| Element D | 0.947 | 0.583 |
| Element E | 0.979 | 0.378 |

All elements showed good correlation with the reference values. Element E (polymer 2 in the gravure layer) showed the best correlation of responses (larger squared correlation coefficient, R$^2$).

EXAMPLE 6

Performance of Elements Prepared with Alternative Latices and Higher Levels of Polymer 2

Gentamicin elements were prepared which contained the cationic polymer 2 at 0.2 g/m$^2$ coated by the gravure process on top of the spread layer. New elements were prepared which were identical to Element E except that the latices, poly(methyl acrylate) (latex 2) (Element F) or poly(methyl acrylate-co-decaethylene monomethacrylate) 94/6 wt ratio (latex 3) (Element G) were coated in the bead spreading layer in place of the standard latex 1. Two additional coatings were prepared which were identical to Elements F and G except that they contained 0.4 g/m$^2$ polymer 2 coated in the receptor layer and also contained an additional 0.2 g/m$^2$ polymer 2 applied in a first gravure layer using the gravure coating method prior to the incorporation of the gentamicin*-HRP and 0.2 g/m$^2$ polymer 2 in a second gravure layer (Elements H and I).

Coatings Compared in Example 6

| Component | Dry Coverage (g/m$^2$) |
|---|---|
| 5) Labeled Ligand Gravure Layer II | |
| Gentamicin*-HRP | .000024 |
| MOPS, pH 7.0 | .0045 |
| Bovine Serum Albumin | .000215 |
| Polyacrylamide | .00108 |
| TRITON TX-100 | .0043 |
| 3',5'-dichloroacetanilde | .00995 |
| Carboxymethylated-apo-HRP | 0.010 |
| Magenta Dye | .0538 |
| polymer 2* | .20 |
| 4) Gravure Layer I | |
| MOPS, pH 7.0 | .0045 |
| Bovine Serum Albumin | .000215 |
| Polyacrylamide | .00108 |
| TRITON TX-100 | .0043 |
| 3'5'-dichloroacetanilide | .00995 |
| Carboxymethylated-apo-HRP | 0.010 |
| polymer 2* | .20 |
| 3) Bead Spreading Layer | |
| TES, pH 7.0 | .219 |
| 3'5',-dichloroacetanilide | .220 |
| Dimedone | .450 |
| latex 1,2, or 3 | 2.583 |
| Poly (m-& p vinyltoluene (64:36)-co-methacrylic | 130 |

| Component | Dry Coverage (g/m²) |
|---|---|
| acid) beads | |
| Bovine Serum Albumin | 1 |
| Glycerol | 2 |
| Mannitol | 1 |
| Vanadyl Sulfate | .040 |
| 2) Receptor Layer | |
| TES, pH 7.0 | .10 |
| TRITON TX-100 | .02 |
| Triarylimidazole leuco dye dispersion | .20 |
| polymer 2* | .40 |
| Anti-gentamicin beads | .10 |
| polymer microgel A | 0.5 |
| 1) Gelatin Layer | |
| Gelatin | 10 |
| TES, pH 7.0 | 4.58 |
| 3',5'-dichloroacetanilide | .44 |
| TRITON TX-100 | .02 |
| BVSME hardener | .15 |

Element E contained latex 1 in the BSL (bead spread layer) and contained polymer 2 only in layer 5. (Layer 4 was not coated.)
Element F contained latex 2 in the BSL and contained polymer 2 only in layer 5. (Layer 4 was not coated.)
Element G contained latex 3 in the BSL and contained polymer 2 only in layer 5. (Layer 4 was not coated.)
Element H contained latex 2 in the BSL and polymer 2 in the receptor layer and in both gravure layers.
Element I contained latex 3 in the BSL and polymer 2 in the receptor layer and in both gravure layers.

These elements were tested with the human serum based calibrator fluids described in Example 1; however, gentamicin*-HRP was not added to the calibrator fluids because the label was incorporated directly into the element. The elements were tested as described in Example 1. The results are shown below:

| Gentamicin (μg/mL) | Element E latex 1 0.2 g/m² poly 2 | Element F latex 2 0.2 g/m² poly 2 | Element G latex 3 0.2 g/m² poly 2 | Element H latex 2 0.8 g/m² poly 2 | Element I latex 3 0.8 g/m² poly 2 |
|---|---|---|---|---|---|
| 0 | 0.233 | 0.220 | 0.260 | 0.192 | 0.229 |
| 0.7 | 0.227 | 0.195 | 0.233 | 0.148 | 0.172 |
| 1.2 | 0.202 | 0.162 | 0.195 | 0.114 | 0.127 |
| 3.2 | 0.122 | 0.077 | 0.105 | 0.051 | 0.057 |
| 5.3 | 0.086 | 0.045 | 0.067 | 0.029 | 0.032 |
| 7.6 | 0.067 | 0.031 | 0.049 | 0.019 | 0.021 |
| 10.4 | 0.051 | 0.020 | 0.034 | 0.011 | 0.013 |
| 14.2 | 0.043 | 0.015 | 0.026 | 0.008 | 0.009 |

All of the elements shown above exhibit acceptable dose response curves over the concentration range of gentamicin measured. The two elements which contain latex 2 (Element F) and latex 3 (Element G) in place of the standard latex 1 (Element E) exhibit a steeper slope at the lower concentrations of gentamicin. The two elements which contain 0.8 g/m² polymer 2 (Elements H and I) exhibit even steeper slopes. The elements prepared with the latex 2 and 3 latices exhibit lower background rates than the latex 1 element.

EXAMPLE 7

Composite Cart Precision of Elements A and H

Composite carts were generated for two elements (Element A and Element H), at a 1% rate. Composite carts are made during mounting of a coating slit into slides. A slide was taken at periodic intervals as a representative sample of that mounting event and of the coating. A 1% rate indicates that one slide is set aside for testing after each 100 consecutive slides were made. These composite slides were then placed into a composite cart. A composite estimate of assay precision (which includes a contribution from slit length variability using the slides from a composite cart) was then obtained. The precision of Element A was tested with a human serum based fluid. Element H was tested with a bovine serum based fluid. The gentamicin concentration in both fluids was approximately 2.5 μg/mL. The measured rates were translated into estimated gentamicin concentration using the calibration generated from the data obtained in the previous examples. The results are shown below:

| | Avg. Estimated Conc. (μg/mL) | SD | % CV |
|---|---|---|---|
| Element A | 3.40 | 0.135 | 3.97 |
| Element H | 2.37 | 0.03 | 1.25 |

Element H prepared with 0.8 g/m² polymer 2 and latex 2 exhibits approximately 3× greater precision than Element A.

EXAMPLE 8

Comparison of the Performance of Elements E, H, and I Using Patient Samples

Three of the elements previously described (E, H and I) were evaluated using 46 patient samples in which the gentamicin concentrations were determined using the COBAS FP fluorescence polarization immunoassay. The patient samples were tested as described in Example 3. The results are shown below:

| | $R^2$ | Sy.x |
|---|---|---|
| Element E | 0.975 | 0.408 |
| Element H | 0.983 | 0.338 |
| Element I | 0.983 | 0.340 |

All three elements show good correlation ($R^2$) with the COBAS FP assay values.

EXAMPLE 9

Stability of Elements A, H, and I

Three of the elements described previously (A, H, and I) were tested for simulated on analyzer stability (OAS) by incubating the coatings at 70° C. and 33% RH for one week prior to testing. The fluids used for testing Element A was human serum based containing gentamicin at 1.4 and 7.9 μg/mL. The fluids used for testing Elements H and I were bovine serum based containing gentamicin at 2.2, 4.7, and 9.0 μg/mL. The results obtained after one week of incubation were compared to control coatings that had been stored under the standard conditions (frozen). Twelve replicates of each fluid were tested on each element. Bias is defined as the difference between the average predicted gentamicin concentration of the control elements and the elements which had been incubated at 70° C./33% RH for one week. The results are shown below:

|  | Fluid A | | Fluid B | |
| --- | --- | --- | --- | --- |
|  | Conc. (μg/mL) | Bias (μg/mL) | Conc. (μg/mL) | Bias (μg/mL) |
| Element A | 1.44 | 0.37 | 7.86 | 0.45 |
| Element H | 2.2 | 0.06 | 9.0 | 0.076 |
| Element I | 2.2 | 0.024 | 9.0 | −0.13 |

Elements H and I exhibit improved stability compared to Element A. Element A exhibits a substantial positive predicted concentration bias with fluids A and B compared to elements H and I.

EXAMPLE 10

Performance of Tobramycin Elements Using the Element G Structure

Tobramycin assay elements were prepared using the same format described for Gentamcin assay elements in Example 4 (Element G). These elements differed from Element G only by the substitution of tobramycin-HRP for gentamicin*-HRP and anti-tobramycin antibody beads for anti-gentamicin antibody beads. Also, 0.85 g/m² BSA (bovine serum albumin) and 0.15 g/m² BgG (bovine gamma globulin) were incorporated into the bead spread layer instead of 1.0 g/m² BSA. These elements (Element J, K, and L) contained three different immobilized tobramycin antibodies incorporated into the receptor layer at a dry coverage of 0.10 g/m². All three elements contained tobramycin-HRP incorporated into the elements via the gravure process at 0.000008 g/m².

These elements were tested with human serum based calibrator fluids which contained tobramycin ranging in concentration from 0.12 to 17.5 μg/mL. These fluids were tested as described in Example 3. The results are shown below:

|  | Rate Dt/min | | |
| --- | --- | --- | --- |
| Tobramycin (μg/mL) | Element J | Element K | Element L |
| 0.1 | 0.140 | 0.135 | 0.120 |
| 0.9 | 0.128 | 0.113 | 0.088 |
| 3.7 | 0.085 | 0.068 | 0.048 |
| 7.8 | 0.056 | 0.043 | 0.029 |
| 10.8 | 0.042 | 0.030 | 0.021 |
| 17.5 | 0.028 | 0.021 | 0.016 |

All three tobramycin assay elements prepared using a format described previously for gentamicin (Element G) exhibit acceptable dose response curves with very low background rates over the concentration range of tobramcyin tested.

The foregoing examples show:

1) Elements prepared according to this invention exhibit steeper dose response curves and lower background rates than elements that do not contain charged materials of the present invention.

2) Charged materials can be incorporated into a variety of locations and provide good assay performance.

3) Elements prepared with charged materials of this invention incorporated via the gravure process provide particularly improved correlation with reference samples.

4) Elements made according to this invention exhibit good cart precision, composite precision, patient accuracy, and stability relative to those of the prior art.

We claim:

1. An assay element for analyzing a charged aminoglycoside analyte comprising;

a) a support;

b) an immobilized receptor capable of binding the aminoglycoside analyte; and c) a polymer on said support having a net charge that is the same as that of the aminoglycoside analyte to repel analyte not bound to the receptor.

2. The assay element of claim 1 wherein the polymer has a net positive charge.

3. The assay element of claim 2 wherein said polymer is made from monomers comprising 20–80% wt. (based on total weight of all monomers) monomers having a net positive charge and about 80–20% wt (based on total weight of all monomers) hydrophilic, non-ionic monomers.

4. The assay element of claim 2 wherein said polymer is made is made from a monomer comprising a quaternary nitrogen.

5. The assay element of claim 4, wherein said monomers are selected from the group consisting of:

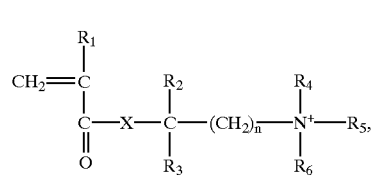

(I)

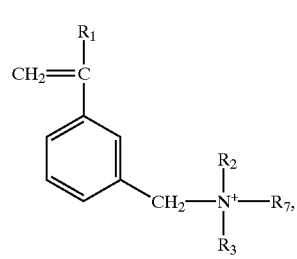

(II)

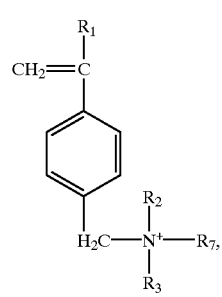

(III)

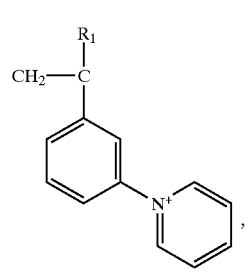

(IV)

-continued

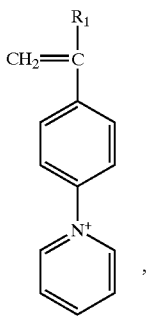 (V)

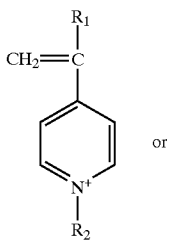 or (VI)

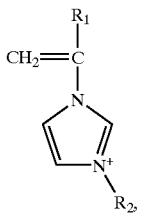 (VII)

and a monomer of formula

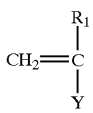 (VIII)

wherein X is NH or O; $R_1$ is H or $CH_3$; $R_2$, $R_3$, $R_4$, $R_5$ and $R_6$ are independently, H, $CH_3$, $CH_2CH_3$, $R_7$ is H, $CH_3$, $CH_2CH_3$ or cyclohexyl; Y is $CONHCH_2CH_2CH_3$, $CONHCH(CH_3)_2$, $COOCH_2CH_2OH$, or 2-pyrrolidinone-1-yl; and n is 0, 1 or 2.

6. The assay element of claim 5 wherein the polymer comprises the monomer of formula (I) and X is NH, $R_1$, $R_4$, $R_5$ and $R_6$ are $CH_3$, $R_2$ and $R_3$ are H, and n=2.

7. The assay element of claim 1 wherein the polymer is poly(acrylamide-co-N-(3-methacrylamidopropyl)-N,N,N-trimethylammonium chloride.

8. The assay element of claim 1 wherein the element is a dry analytical element.

9. The assay element of claim 1, wherein the charge on the aminoglycoside analyte arises from a linking group attached to the analyte or from a label appended thereto.

10. The assay element of claim 1 wherein the analyte is tobramycin or gentamicin, Streptomycin, Streptomycin B, Neomycin, Amikacin, Kanamycin A&B, Dibekacin, Netilmicin, or Spectimycin.

11. The assay element of claim 1 wherein said element is a dry analytical element further comprising:

i) a receptor zone comprising the immobilized receptor;
ii) a label zone comprising a labeled reactant wherein the labeled reactant is a labeled analyte or labeled analog of the analyte, or a labeled receptor specific to the analyte; and
iii) a spreading zone.

12. A method for determining the presence or amount of a charged aminoglycoside analyte in a sample, comprising the steps of:

A) contacting the sample with
  a) an element comprising
    i) an immobilized receptor specific to the analyte,
    ii) a polymer having a net charge which is the same as that of the analyte,
  b) a labeled reactant wherein said labeled reactant is a labeled analyte or labeled analog of the analyte, or a labeled receptor specific to the analyte;
B) separating free labeled reactant from bound labeled reactant; and
C) determining the bound labeled reactant as a measure of the presence or amount of the analyte.

13. The method of claim 12 where the polymer is made from monomers comprising 20–80% wt. (based an total weight of all monomers) monomers having a net positive charge and about 80–20% wt (based on total weight of all monomers hydrophilic, non-ionic monomers.

14. The method of claim 12 where the polymer is made from a monomer comprising a quaternary nitrogen having one or more $C_1$ to $C_3$ alkyl groups, or a monomer comprising a mono- or poly-cyclic ring of between 5 to 14 ring atoms selected from C, S, N, or O, provided at least one of the ring atoms is a quaternary nitrogen.

15. The method of claim 14 wherein the polymer is made from monomer of formula:

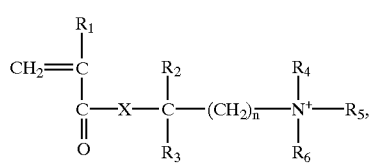 (I)

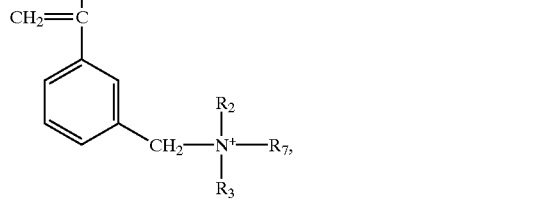 (II)

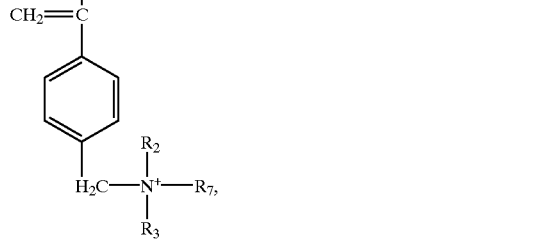 (III)

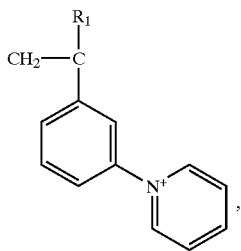

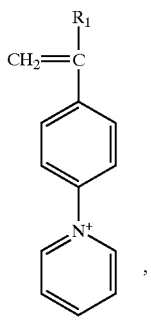

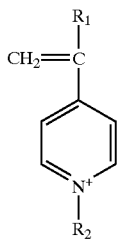 or (IV)

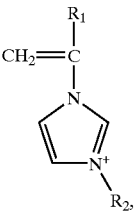

(V)

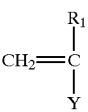

(VI)

(VII)

and a non-ionic hydrophilic monomer of forumula $$CH_2 = \overset{R_1}{\underset{Y}{C}}$$ (VIII)

wherein X is NH or O; $R_1$ is H or $CH_3$; $R_2$, $R_3$, $R_4$, $R_5$ and $R_6$ are independently H, $CH_3$, $CH_2CH_3$, $R_7$ is H, $CH_3$, $CH_2CH_3$ or cyclohexyl; Y is $CONHCH_2CH_2CH_3$, $CONHCH(CH_3)_2$, $COOCH_2CH_2OH$, or 2-pyrrolidinone-1-yl; and n is 0, 1 or 2.

16. The method of claim 15 wherein the polymer is poly(acrylamide-co-N-(3-methacrylamidopropyl)-N,N,N-trimethylammonium chloride.

* * * * *